United States Patent [19]

Kómives et al.

[11] Patent Number: 4,948,420
[45] Date of Patent: * Aug. 14, 1990

[54] HERBICIDAL ARYLOXY PHENOXY ACYL MALONATES

[75] Inventors: Tamás Kómives; Ferenc Dutka, both of Budapest; István Barta, Paty; István Jablonkai, Budapest; Ágnes Hulesch, Budapest; Ferenc Bihari, Budapest; Gyula Eifert, Dunaharaszt; Péter Bohus, Budapest; Katalin Tromfos, Budapest; Ágnes Mészáros née Szekrenyesi, Budapest; István Küronya, Budapest, all of Hungary

[73] Assignees: Budapesti Vegyimuvek; MTA Kozponti Mediai Kutato Intezet, both of Budapest, Hungary

[*] Notice: The portion of the term of this patent subsequent to Aug. 23, 2005 has been disclaimed.

[21] Appl. No.: 231,883

[22] Filed: Aug. 12, 1988

Related U.S. Application Data

[63] Continuation-in-part of Ser. No. 910,892, Sep. 23, 1986, Pat. No. 4,765,825.

[30] Foreign Application Priority Data

Oct. 1, 1985 [HU] Hungary .................. 3798/85
Jun. 27, 1986 [HU] Hungary .................. 3798/85

[51] Int. Cl.$^5$ ............... C07D 213/57; C07D 213/643; A01N 43/40
[52] U.S. Cl. .................................. 71/94; 546/288; 546/302
[58] Field of Search ................ 546/302, 288; 71/94

[56] References Cited

U.S. PATENT DOCUMENTS 4,765,825 8/1988 Komives et al. ............ 71/94

OTHER PUBLICATIONS

Chemical Abstracts, vol. 107(13), 115, 370-R, Sep. 28, 1987.

*Primary Examiner*—Alan L. Rotman
*Attorney, Agent, or Firm*—Herbert Dubno; Jonathan Myers

[57] ABSTRACT

The invention relates to new aryloxy phenoxy acyl malonates of the Formula I

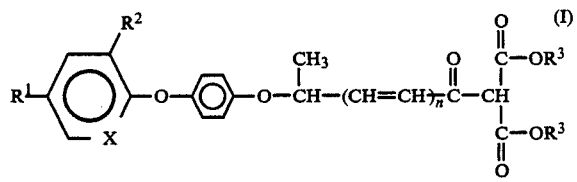

a process for the preparation thereof and herbicidal compositions comprising the same.

In the Formula I
$R^1$ stands for hydrogen, halogen, trifluoromethyl, trifluoromethoxy or cyano;
$R^2$ represents hydrogen, halogen, or methyl; and
$R^3$ is $C_{1-4}$ alkyl, and the $R^3$ substitutents may be the same or different,
X stands for —N= or —CH= and
n is 0 or 1.

The new compound of the Formula I possess valuable herbicidal properties.

4 Claims, No Drawings

HERBICIDAL ARYLOXY PHENOXY ACYL MALONATES

CROSS REFERENCE TO RELATED APPLICATIONS

This application is a continuation-in-part of copending application Ser. No. 910,892, filed Sept. 23, 1986, now U.S. Pat. No. 4,765,825.

This invention relates to new aryloxy phenoxy acyl malonates, a process for the preparation thereof, herbicidal compositions comprising the same and a method for combatting weeds by using the said compositions.

It is known that certain phenoxy-phenoxy-carboxylic acid derivatives possess herbicidal properties. Such compounds are disclosed in Hungarian patent No. 178,245 and U.S. Pat. No. 4,448,966.

According to an aspect of the present invention there are provided new aryloxy phenoxy acyl malonates of the Formula I

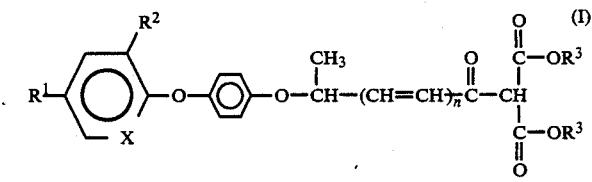

(wherein
$R^1$ stands for hydrogen, halogen, trifluoromethyl, trifluoromethoxy or cyano;
$R^2$ represents hydrogen, halogen or methyl;
$R^3$ is $C_{1-4}$ alkyl; and the $R^3$ substituents may be the same or different,
X stands for —N= or —CH= and
n is 0 or 1).

The new compounds of the Formula I differ from the known derivatives in the structure of the moiety attached to the carbonyl group.

The new compounds of the Formula I exhibit a stronger herbicidal effect than the known derivatives, particularly on pre-emergent application. The compounds of the present invention are particularly suitable for the selective control of grassy weeds in various cultivated plants, especially in dicotyledonous cultures.

A preferred compound of the Formula I is the derivative in which
$R^1$ and $R^2$ are chlorine; $R^3$ stands for ethyl;
X is —CH= and n is 0.

In a further preferred compound of the Formula I $R^1$ is trifluoromethyl; $R^2$ stands for hydrogen; $R^3$ is ethyl; X stands for —N= and n is 0.

The term "$C_{1-4}$ alkyl" relates to straight or branched chain alkyl groups having 1-4 carbon atoms (e.g. methyl, ethyl, n-propyl, isopropyl, N-butyl).

According to a further aspect of the present invention there are provided herbicidal compositions comprising as active ingredient in an amount of 0.01-95% by weight at least one compound of the Formula I (wherein $R^1$, $R^2$, $R^3$, X and n are as stated above) in admixture with suitable solid or liquid carriers or diluents and optionally auxiliary agents, (e.g. surfactants, antifoam, antifreezing, adhesive agents).

The compositions of the present invention may be solid or liquid and may be finished in usual forms (e.g. powder mixture, dusting powder, granule, paaste, emulsion, suspension, solution, spray, concentrate etc.). The compositions comprise diluents and carriers and auxiliary agents generally used in agriculture and plant protection.

The solid carriers may be mineral or synthetic materials, e.g. China-clay, siliceous earth, talc, attapulgite, diatomaceous earth, alumina, silicic acid and various silicates. As liquid diluent e.g. mineral oil fractions (e.g. gas oil, or kerosine), oils of animal or vegetable origin, aromatic, aliphatic or alicyclic hydrocarbons (e.g. benzene, toluene, xylene, cyclohexane, tetrahyronaphthalene) and derivatives thereof (e.g. chlorobenzene, alkyl naphthalenes, cyclohexanol, butanol) or strongly polar solvents (e.g. dimethyl formamide, dimethyl sulfoxide, N-methylpyrrolidone, water) may be used.

The surfactants (emulsifying, dispersing, wetting, antifoaming or antiaggregating agents) may be of ionic or non-ionic character. As ionic surfactants the following compounds may be used: salts of saturated or unsaturated carboxylic acids; sulfonates of aliphatic, aromatic or aliphatic-aromatic hydrocarbons; sulfonates of alkyl, aryl and aralkyl alcohols; sulfonates of alkyl, aryl and aralkyl carboxylic acids and esters and ethers thereof; sulfonates of condensation products of phenols, cresols or naphthalene; sulfated oils of animal or vegetable origin; alkyl, aryl or aralkyl phosphate esters; sulfates and phosphates of polyglycol ethers of ethylene oxide formed with fatty alcohols or alkyl phenols, etc.

As non-ionic surfactants e.g. the following compounds may be used: condensation products of ethylene oxide and fatty alcohols; alkyl aryl polyglycol ethers; polymers of ethylene oxide and/or propylene oxide and derivatives thereof; alkyl cellulose.

As antifoam agents e.g. ethylene oxide/propylene oxide condensation products having a low molecular weight; aliphatic alcohols; special silicone oils or fatty acid amides may be used.

As adhesive or thickening agent e.g. alkaline earth metal soaps; salts of sulfosucconic acid esters; natural or synthetic macromolecular materials which are soluble or swellable in water may be used.

As antifreezing agent e.g. ethylene glycol, propylene glycol or glycerol may be used.

The herbicidal compositions of the present invention may be prepared by known methods of the pesticidal industry by admixing at least one compound of the Formula I with suitable inert solid and/or liquid carriers or diluents or optionally with auxiliary agents.

According to a still further aspect of the present invention there is provided a method for controlling weeds which comprises applying onto the objects to be protected—preferably onto plants, parts of plants or soil—an effective amount of a compound of the Formula I or a composition comprising the same.

According to a still further aspect of the present invention there is provided a process for the preparation of compounds of the Formula I (wherein $R^1$, $R^2$, $R^3$, X and n are as stated above) which comprises:
(a) reacting an aryloxy phenoxy carboxylic acid derivative of the Formula II

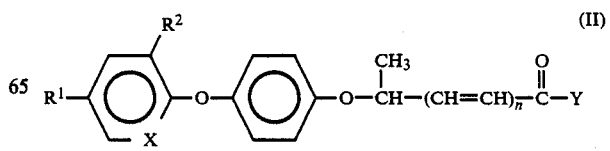

(wherein $R^1$, $R^2$, n and X are as stated above and Y represents halogen, cyano or $C_{1-6}$ alkyl-carbonyloxy) with a metal derivative of a malonate of the Formula III

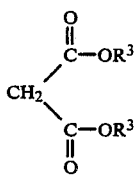
(III)

(wherein $R^3$ is as stated above) or in the presence of a metal compound with a malonate of the Formula III; or (b) reacting an aryloxy phenol of the Formula IV

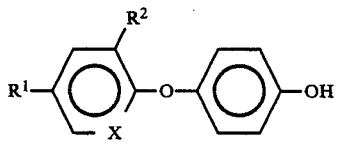
(IV)

(wherein $R^1$, $R^2$, and X are as stated above) or an alkali metal salt thereof with a halogenic compound of the Formula V

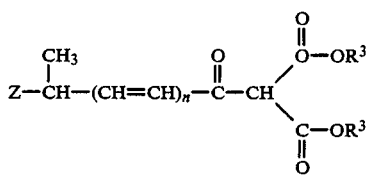
(V)

(wherein n and $R^3$ are as stated above and Z is halogen); or (c) reacting an aryl compound of the Formula VI

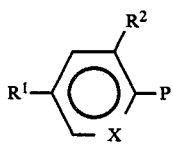
(VI)

with an aryloxy derivative of the Formula VII

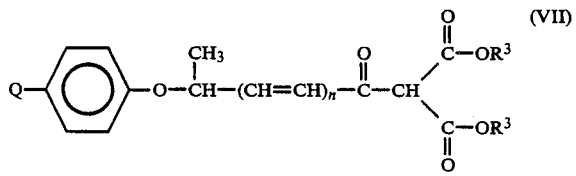
(VII)

(wherein $R^1$, $R^2$, $R^3$, n and X are as stated above and if Q stands for hydroxy or alkali metal oxy P represents halogen or if Q stands for halogen P represents hydroxy or alkali metal oxy).

According to process (a) it is preferred to use a sodium, potassium or magnesium derivative of the malonate of the Formula III. If the malonic acid derivative of the Formula III is used per se it is preferred to carry out the reaction in the presence of a magnesium compound particularly magnesium chloride as metal compound. Y as halogen stands preferably for chlorine. The reaction may be carried out preferably in an inert solvent. As solvent advantageously a hydrocarbon (e.g. benzene, toluene or xylene), an ether (e.g. diethyl ether, 1,2-dimethoxy ethane, tetrahydrofuran or dioxane) an amide (e.g. dimethyl formamide, hexamethyl phosphoric acid triamide) a ketone (e.g. acetone or diethyl ketone) or a nitrile (e.g. acetonitrile) etc. may be used.

The malonic acid derivatives of the Formula III are reacted in the form of a metal salt thereof with the compound of the Formula II. The metal salts of the malonates may be prepared previously e.g. by reacting a malonate of the Formula III with an alkali or alkaline earth metal compound. According to an other alternative the reaction of the compounds of the Formula II and III is carried out in the presence of a metal compound—preferably magnesium chloride. In this case the metal salt of the malonate of the Formula III is in situ formed in the reaction mixture.

The reaction may be accomplished at a temperature between $-10°$ C. and $+180°$ C., preferably at $30°-100°$ C. The desired compound is separated by known methods after the removal of the by-products formed.

The malonates of the Formula III and metal salts thereof and the starting materials of the Formula II are partly known compounds. Such compounds are disclosed in U.S. Pat. Nos. 4,263,040 and 4,227,009 and in the publications Org. Synth. Coll. Vol. IV 285 and J. Org. Chem. 50, 2622 (1985). The new compounds of the Formula II may be prepared in an analogous manner to the process described in the said publications.

According to processes (b) and (c) the compounds of the Formulae IV and V, and VI and VII, respectively, are reacted preferably in the presence of an inert solvent or diluent. As reaction medium the solvents disclosed above in connection with process (a) may be used. It is preferred to work in the presence of an acid binding agent e.g. an alkali hydroxide, alkali carbonate, alkali ethylate or alkali tert. butylate (e.g. sodium or potassium hydroxide, carbonate, ethylate or tert. butylate) or any suitable organic base (e.g. triethyl amine).

Further details of the present invention are to be found in the following Examples without limiting the scope of protection of the said Examples.

EXAMPLE 1

Preparation of diethyl-2-[4'-(2'',4''-dichloro-phenoxy)-phenoxy]-propionyl-malonate (a) A 50% etheral solution of 35 g of 2-[4'-(2'',4''-dichloro-phenoxy)-phenoxy]-propionyl-chloride is added under stirring dropwise to a mixture of diethyl-ethoxy-magnesium-malonate prepared from 17.6 g of diethyl malonate and 50 ml of ether. The addition of the acid chloride having been completed the reaction mixture is heated to boiling for an hour, cooled to room temperature and washed successively with 100 ml of 5% sulfuric acid, 100 ml of a 6% sodium bicarbonate solution and 100 ml of water. The etheral phase is evaporated, the excess of the malonic acid ester is distilled off, the residue is admixed with 100 ml of benzene, subjected to chromatography on a silica column and eluted with 50 ml of benzene. The united eluates are evaporated. Thus 35 g of the desired compound are obtained in the form of a slowly solidifying product. Mp.: 46°-50° C. Yield 75%.

Into a 500 ml flask equipped with a stirrer and a dropping funnel 9.52 g of anhydrous magnesium chloride and 100 ml of anhydrous acetonitrile are introduced. To the heterogeneous mixture 16.0 g of diethyl malonate are added, the reaction flask is placed into an ice bath whereupon 28 ml of triethyl amine are added. To the solution at 0° C. 35 g of 2-[4'-(2",4"-dichloro-phenoxy)-phenoxy]-propionyl-chloride are added dropwise within 15 minutes. The reaction mixture is stirred at 0° C. for an hour and at room temperature for 12 hours whereupon it is cooled to 0° C. and 60 ml of a 5M hydrochloric acid solution are added. The solution thus obtained is extracted three times with 100 ml of ether each, the united extracts are dried over magnesium sulfate and the solvent and the traces of diethyl malonate are removed. The slightly yellow oil thus obtained slowly solidifies. Thus 41.8 g of the desired compound are obtained, yield 89%, mp.: 46°–50° C.

(c) 25.5 g of 4-(2',4'-dichloro-phenoxy)-phenol and 25.1 g of diethyl-2-chloro-propionyl-malonate are dissolved in 150 ml of dimethyl sulfoxide, 13.8 g of potassium carbonate are added and the reaction mixture is stirred at 60° C. for 48 hours. The reaction mixture is filtered and the filtrate is evaporated. The residue is dissolved in 100 ml of benzene, washed successively with 100 ml of a saturated aqueous sodium bicarbonate solution and water. The benzene solution is evaporated. Thus 32 g of the desired compound are obtained, yield 68%.

(d) 27.7 g of sodium-4-(2',4'-dichloro-phenoxy)-phenolate and 25.1 g of diethyl-2-chloro-propionyl-malonate are dissolved in 150 ml of dimethyl sulfoxide and the reaction mixture is stirred at 60° C. for 48 hours under stirring. The reaction mixture is filtered and the filtrate is evaporated. The residue is dissolved in 100 ml of benzene and washed successively with 100 ml of a saturated aqueous sodium hydrogen carbonate solution and water. The benzene solution is evaporated. Thus 30 g of the desired compound are obtained, yield 61%.

EXAMPLE 2

Preparation of dimethyl-2-[4'-(4"-trifluoromethyl-phenoxy)-phenoxy]-propionyl-malonate A 50% etheral solution of 39 g of 2-[4'-(4"-trifluoromethyl-phenoxy)-phenoxy]-propionyl-bromide is added dropwise under stirring to a mixture of dimethyl-ethoxy-magnesium-malonate prepared from 14.5 g of dimethyl malonate and 50 ml of ether. The addition of the acid bromide having been completed the reaction mixture is heated to boiling for an hour and worked up as described in Example 1. Thus 37 g of the desired compound are obtained in the form of a yellow viscous oil which solidifies on standing, mp.: 40°–44° C. Yield 84%.

EXAMPLE 3

Preparation of diethyl-2-[4'-(4"-cyano-phenoxy)-phenoxy]-malonate (a) A mixture of 30 g of 2-[4'-(4"-cyano-phenoxy)-phenoxy]-propionyl chloride and 30 ml of ether is added dropwise to a 35% etheral solution of magnesium diethyl malonate prepared from 17.6 g of diethyl malonate. The addition of the acid chloride having been completed the reaction mixture is heated to boiling for an hour and worked up as described in Example 1. Thus 30 g of the desired compound are obtained in the form of a viscous oil which solidifies on standing and melts at 42°–46° C. Yield 72%.

(b) 11.9 g of cyano-phenol and 32.6 g of diethyl-2-(4'-fluoro-phenoxy)-propionyl-malonate are dissolved in 150 ml of dimethyl sulfoxide, whereupon 13.8 g of potassium carbonate are added and the reaction mixture is stirred at 60° C. for 6 hours. The reaction mixture is filtered and the filtrate is evaporated. Thus 36 g of the desired compound are obtained, yield 86%.

EXAMPLE 4

Preparation of diethyl-2-[4'-(5"-trifluoromethyl-2"-pyridyloxy)-phenoxy]-propionyl-malonate (a) Into a 250 ml round-bottomed flask equipped with a magnetic stirrer, a dropping funnel and a calcium chloride tube 100 ml of toluene, 10.1 g of triethyl amine and 33 g of 2-[4'-(5"-trifluoromethyl-2"-pyridyloxy)-phenoxy]-propionic acid are weighed in. The reaction mixture is cooled below 0° C. and 10.8 g of ethyl chloro formiate are added dropwise at a rate that the temperature should be between −1° C. and 0° C. The thick suspension thus obtained is stirred for a further period of 20 minutes. To the above mixture under stirring a mixture of 50 ml of ether and diethyl-ethoxy magnesium malonate prepared from 17.6 g of diethyl malonate is added at a rate that the temperature should not exceed 0° C. The reaction mixture is allowed to stand at room temperature for 16 hours and worked up as described in Example 1. Thus 42 g of the desired compound are obtained in the form of a thick yellow oil, yield 90%; $n_D^{24} = 1.4960$.

(b) 18.1 g of 2-chloro-4-trifluoromethyl-pyridine and 32.4 g of diethyl-2-(4'-hydroxy-phenoxy)-propionyl-malonate are dissolved in 150 ml of dimethyl formamide, whereupon the reaction mixture is stirred in the presence of 13.8 g of potassium carbonate at 60° C. for 48 hours. The reaction is purified on a silica column as described in Example 1a. Thus 30 g of the desired compound are obtained, yield 64%.

EXAMPLES 5–12

The compounds of the Formula I enumerated in Table I are prepared in an analogous manner to the processes disclosed in Examples 1–4.

TABLE 1

| Example No. | Substituents of the Formula I | | | | Physical Constants |
|---|---|---|---|---|---|
| | X | $R^1$ | $R^2$ | $R^3$ | n | Mp. °C. |
| 5 | CH | Cl | H | $C_2H_5$ | O | 35–38 |
| 6 | CH | $CF_3$ | H | $C_2H_5$ | O | oil |
| 7 | CH | $CF_3O$ | H | $C_2H_5$ | O | oil |
| 8 | CH | $CF_3$ | $CH_3$ | $C_2H_5$ | O | oil |
| 9 | CH | Br | H | $C_2H_5$ | O | 37–41 |
| 10 | N | H | H | $C_2H_5$ | O | oil |
| 11 | N | Cl | H | $C_2H_5$ | O | oil |
| 12 | N | Cl | Cl | $C_2H_5$ | O | 33–36 |

EXAMPLE 13

Preparation of diethyl-4-[4'-(4"-trifluoromethyl-phenoxy)-phenoxy]-2-pentenoyl-malonate One proceeds in an analogous manner to the process disclosed in Example 4 by reacting 4-[4'-(4"-trifluoromethyl-phenoxy)-phenoxy]-2-pentenoic acid at first with 12 g of pivaloyl chloride and thereafter with diethyl-ethoxy-magnesium malonate prepared from 17.6 g of diethyl malonate. The reaction mixture is worked up. 43 g of of the viscous oily desired compound are obtained which turns to a faint yellow crystalline product on standing. Mp.: 52°–55° C., yield 87%.

EXAMPLE 14

Preparation of dimethyl-4-[4'-(2",4"-dichloro-phenoxy)-phenoxy]-2-pentenoyl-malonate From 4.6 g of sodium, 26 g of dimethyl malonate and 60 ml of ether a dimethyl sodium malonate solution is prepared which is added dropwise under stirring to a mixture of 37 g of 4-[4'-(2",4"-dichloro-phenoxy)-phenoxy]-2-pentenoyl chloride and 50 ml of ether. The reaction mixture is heated to boiling for 2 hours and worked up as described in Example 1. Thus 37 g of the faint yellow crystalline desired compound are obtained, yield 79%, mp.: 60°–63° C.

EXAMPLES 15–19

In an analogous manner to the process described in Examples 1–4 and 13–14 the compounds of the Formula I enumerated in Table II are prepared.

TABLE II

| Example No. | Substituents of the Formula I | | | | | Physical Constants |
|---|---|---|---|---|---|---|
| | X | $R^1$ | $R^2$ | $R^3$ | n | Mp. °C. |
| 15 | CH | Cl | H | $C_2H_5$ | 1 | 42–45 |
| 16 | CH | $CF_3O$ | H | $C_2H_5$ | 1 | 36–38 |
| 17 | CH | CN | H | $C_2H_5$ | 1 | oil |
| 188 | N | $CF_3$ | H | $C_2H_5$ | 1 | oil |
| 19 | CH | $CF_3$ | Cl | $CH_3 C_3H_7$ | 1 | oil |

PREPARATION OF HERBICIDAL COMPOSITIONS

EXAMPLE 20

Granules having an active ingredient content of 0.01%

2.3 g of technical grade compound No. 1 (purity: 89%) are dissolved in 97.7 g of methylene chloride to yield a solution having a concentration of 2% by weight. An acidic pearl siliceous earth carrier prepared from 4000 g of diatomaceous earth are placed into a Loedige 20 type turbine stirrer; the average particle size of the carrier is between 0.5 and 2 mm. 20 g of the active ingredient premix (2% mm/m solution) are sprayed onto the granulated carrier through Tee-Jet 10080 nozzles at a rate of 5 g/minutes, whereby the granules are stirred in the Loedige type stirrer with a velocity of 50 r.p.m. The sorption type granules are packed.

EXAMPLE 21

Sprayable powder having an active ingredient of 95%

240 g of compound No. 2 (purity 97%; previously powdered in a mill equipped with a rotating blade) are admixed with 2.5 g of Cab-O-Sil M5 (amorphous silica; carrier) and 7.5 g of type 1494 dispersing agent (sodium salt of the condensation product of sulfonated cresole and formaldehyde) in a mortar. The powdered mixture is ground in a turbine mill (Alpine LMRS-80) under an injected airpressure of 5 bar and a grinding air pressure of 4.5 bar at a feeding rate of 250 g/h. Although the sprayable powder thus obtained contains no separate wetting agent it is readily wettable, and has a maximal particle size of 20 μm. In a spray having a concentration of 10 g/l the floatability at 30° C. after 30 minutes is as follows:
84% in CIPAC standard D water; and
91% in CIPAC standard A water.

EXAMPLE 22

Emulsifiable concentrate having an active ingredient content of 24%

40 g of Tween 85 (ethoxylated sorbitan trioleate) and 30 g of Sapogenat T-180 (ethoxylated tributyl phenol) emulsifiers and 250 g of technical grade compound No. 7 (purity: 96%) are dissolved in 400 g of cyclohexanone at 40°–45° C. under stirring. When all the components are dissolved the solution of the active ingredient (temperature 40°–45° C.) is poured into a mixture of 200 g of ionexchanged water and 70 g of ethylene glycol under vigorous stirring whereupon the mixture is cooled to 15°–20° C. Before the termination of the stirring period 10 g of Silicon S RE antifoam agent (a 30% emulsion of dimethyl silicone oil) are added to the emulsion and five minutes later the stirring is stopped.

EXAMPLE 23

Biological application of the composition

Grass seeds and seeds of cultivated plants are sown into sand of the riber Danube in plastic boxes (size 10×10×10 cm) and compositions prepared from the emulsifiable concentrates of the test compounds are sprayed onto the surface of the sand (pre-emergent treatment) and three weeks after sowing (post-emergent treatment). The plastic boxes are watered at a rate required for the normal plant growth and are kept in a glass house. The results of the treatment are evaluated after a test period of four weeks and assessed with the aid of a scale from 0 to 10, wherein 0=no symptoms and 10=completely destroyed infected plants (100%).

As reference compounds two commercially available herbicides are used namely dichlofop-methyl [chemical name: methyl-2-[4-(2,4-dichloro-phenoxy)-phenoxy]-propanoate] and fluazifop butyl [chemical name: butyl-2-[4-(5-trifluoromethyl-2-pyridyloxy]-phenoxy-propanoate].

The results are summarized in Table III. It appears from the said data that the activity of the compounds of the present—as the average activity against grassy weeds—is superior to that of the reference compounds, particularly in pre-emergent application.

The tolerance of a number of cultivated plants against the compositions of the present invention has been determined by means of the treating methods disclosed in this Example. It has been found that dicotyledonous cultivated plants tolerate well all the compositions of the present invention and in the herbicidal dose none of the invention compounds cause any phytotoxical symptoms.

TABLE III

Activity data of the compounds of the Formula I on various weeds and cultivated plants in pre-emergent and post-emergent treatment

| Test compound Example No. | Dose kg active ingredient/ha | Alopecurus myosuroides pre | Alopecurus myosuroides post | Lolium perenne pre | Lolium perenne post | digitaria sanguinalis pre | digitaria sanguinalis post | Setaria italica pre | Setaria italica post | Echinochloa crus-galli pre | Echinochloa crus-galli post | soya pre | soya post | bean pre | bean post | pea pre | pea post | lentil pre | lentil post |
|---|---|---|---|---|---|---|---|---|---|---|---|---|---|---|---|---|---|---|---|
| 1 | 0.5 | 6 | 8 | 9 | 9 | 9 | 9 | 9 | 10 | 9 | 9 | 0 | 0 | 0 | 0 | 0 | 0 | 0 | 0 |
| 1 | 1.5 | 10 | 10 | 10 | 10 | 10 | 10 | 10 | 10 | 10 | 10 | 0 | 0 | 0 | 0 | 0 | 0 | 0 | 0 |
| 2 | 0.5 | 4 | 6 | 6 | 7 | 7 | 8 | 6 | 10 | 6 | 7 | 0 | 0 | 0 | 0 | 0 | 0 | 0 | 0 |
| 2 | 1.5 | 8 | 9 | 9 | 9 | 9 | 10 | 10 | 10 | 10 | 10 | 0 | 0 | 0 | 0 | 0 | 0 | 0 | 0 |
| 3 | 0.5 | 5 | 4 | 6 | 5 | 6 | 6 | 6 | 8 | 6 | 6 | 0 | 0 | 0 | 0 | 0 | 0 | 0 | 0 |
| 3 | 1.5 | 8 | 8 | 9 | 9 | 10 | 10 | 9 | 10 | 10 | 10 | 0 | 0 | 0 | 0 | 0 | 0 | 0 | 0 |
| 4 | 0.5 | 8 | 8 | 8 | 9 | 8 | 9 | 10 | 10 | 8 | 8 | 0 | 0 | 0 | 0 | 0 | 0 | 0 | 0 |
| 4 | 1.5 | 10 | 10 | 10 | 10 | 10 | 10 | 10 | 10 | 10 | 10 | 0 | 0 | 0 | 0 | 0 | 0 | 0 | 0 |
| 5 | 0.5 | 8 | 7 | 8 | 8 | 10 | 9 | 10 | 10 | 10 | 10 | 0 | 0 | 0 | 0 | 0 | 0 | 0 | 0 |
| 5 | 1.5 | 5 | 9 | 10 | 10 | 7 | 10 | 7 | 10 | 6 | 8 | 0 | 0 | 0 | 0 | 0 | 0 | 0 | 0 |
| 6 | 0.5 | 8 | 4 | 9 | 5 | 6 | 6 | 10 | 8 | 6 | 6 | 0 | 0 | 0 | 0 | 0 | 0 | 0 | 0 |
| 6 | 1.5 | 3 | 7 | 5 | 8 | 8 | 9 | 6 | 10 | 8 | 9 | 0 | 0 | 0 | 0 | 0 | 0 | 0 | 0 |
| 7 | 0.5 | 6 | 4 | 7 | 9 | 9 | 10 | 8 | 10 | 9 | 10 | 0 | 0 | 0 | 0 | 0 | 0 | 0 | 0 |
| 7 | 1.5 | 8 | 8 | 10 | 10 | 10 | 10 | 10 | 10 | 10 | 10 | 0 | 0 | 0 | 0 | 0 | 0 | 0 | 0 |
| 8 | 0.5 | 10 | 10 | 4 | 5 | 4 | 6 | 6 | 8 | 6 | 6 | 0 | 0 | 0 | 0 | 0 | 0 | 0 | 0 |
| 8 | 1.5 | 3 | 3 | 4 | 7 | 8 | 9 | 6 | 10 | 10 | 10 | 0 | 0 | 0 | 0 | 0 | 0 | 0 | 0 |
| 9 | 0.5 | 4 | 6 | 4 | 3 | 5 | 4 | 8 | 8 | 6 | 8 | 0 | 0 | 0 | 0 | 0 | 0 | 0 | 0 |
| 10 | 0.5 | 2 | 2 | 4 | 3 | 8 | 8 | 5 | 8 | 8 | 8 | 0 | 0 | 0 | 0 | 0 | 0 | 0 | 0 |
| 10 | 1.5 | 4 | 6 | 6 | 8 | 9 | 9 | 8 | 10 | 8 | 9 | 0 | 0 | 0 | 0 | 0 | 0 | 0 | 0 |
| 11 | 0.5 | 5 | 6 | 8 | 8 | 9 | 10 | 5 | 10 | 6 | 10 | 0 | 0 | 0 | 0 | 0 | 0 | 0 | 0 |
| 11 | 1.5 | 8 | 8 | 9 | 9 | 9 | 10 | 8 | 10 | 8 | 10 | 0 | 0 | 0 | 0 | 0 | 0 | 0 | 0 |
| 12 | 0.5 | 8 | 8 | 10 | 10 | 10 | 10 | 9 | 10 | 10 | 10 | 0 | 0 | 0 | 0 | 0 | 0 | 0 | 0 |
| 12 | 1.5 | 10 | 10 | 10 | 10 | 10 | 10 | 10 | 9 | 10 | 10 | 0 | 0 | 0 | 0 | 0 | 0 | 0 | 0 |
| 13 | 0.5 | 4 | 6 | 6 | 7 | 7 | 7 | 7 | 9 | 6 | 7 | 0 | 0 | 0 | 0 | 0 | 0 | 0 | 0 |
| 13 | 1.5 | 8 | 8 | 8 | 9 | 9 | 10 | 9 | 10 | 10 | 10 | 0 | 0 | 0 | 0 | 0 | 0 | 0 | 0 |
| 14 | 0.5 | 10 | 10 | 10 | 10 | 10 | 10 | 10 | 10 | 10 | 10 | 0 | 0 | 0 | 0 | 0 | 0 | 0 | 0 |
| 14 | 1.5 | 10 | 10 | 10 | 10 | 10 | 10 | 10 | 10 | 10 | 10 | 0 | 0 | 0 | 0 | 0 | 0 | 0 | 0 |
| 15 | 0.5 | 10 | 10 | 10 | 10 | 10 | 10 | 10 | 10 | 10 | 10 | 0 | 0 | 0 | 0 | 0 | 0 | 0 | 0 |
| 15 | 1.5 | 10 | 10 | 10 | 10 | 10 | 10 | 10 | 10 | 10 | 10 | 0 | 0 | 0 | 0 | 0 | 0 | 0 | 0 |
| 16 | 0.5 | 10 | 10 | 10 | 10 | 10 | 10 | 10 | 10 | 10 | 10 | 0 | 0 | 0 | 0 | 0 | 0 | 0 | 0 |
| 16 | 1.5 | 10 | 10 | 10 | 10 | 10 | 10 | 10 | 10 | 10 | 10 | 0 | 0 | 0 | 0 | 0 | 0 | 0 | 0 |
| 17 | 0.5 | 10 | 10 | 10 | 10 | 10 | 10 | 10 | 10 | 10 | 10 | 0 | 0 | 0 | 0 | 0 | 0 | 0 | 0 |
| 17 | 1.5 | 10 | 10 | 10 | 10 | 10 | 10 | 10 | 10 | 10 | 10 | 0 | 0 | 0 | 0 | 0 | 0 | 0 | 0 |
| 18 | 0.5 | 10 | 10 | 10 | 10 | 10 | 10 | 10 | 10 | 10 | 10 | 0 | 0 | 0 | 0 | 0 | 0 | 0 | 0 |
| 18 | 1.5 | 10 | 10 | 10 | 10 | 10 | 10 | 10 | 10 | 10 | 10 | 0 | 0 | 0 | 0 | 0 | 0 | 0 | 0 |
| 19 | 0.5 | 2 | 7 | 3 | 8 | 3 | 8 | 4 | 10 | 5 | 10 | 0 | 0 | 0 | 0 | 0 | 0 | 0 | 0 |
| 19 | 1.5 | 4 | 10 | 5 | 10 | 6 | 10 | 7 | 10 | 6 | 10 | 0 | 0 | 0 | 0 | 0 | 0 | 0 | 0 |
| dichlorofop metil reference compound | 0.5 | 3 | 8 | 4 | 9 | 4 | 9 | 5 | 10 | 5 | 6 | 0 | 0 | 0 | 0 | 0 | 0 | 0 | 0 |
| fluazifop-butil reference compound | 1.5 | 4 | 10 | 6 | 10 | 6 | 10 | 8 | 10 | 8 | 10 | 0 | 0 | 0 | 0 | 0 | 0 | 0 | 0 |

EXAMPLE 24

Test for the comparison of the activity of 2-[4'-(5''-trifluoromethyl-2''-pyridyloxy)-phenoxy]-propionyl-malonate (compound No. 4) and 2-[4'-(5'''-trifluoromethyl-2''-phenoxy)-phenoxy-propionyl-malonate (compound No. 6), the latter also disclosed in Japanese Patent Application No. 56/046,842 to KANESHO.

Seeds of dicotyledonus weeds are sown into sand of the river Danube in plastic boxes (size 10×10×10 cm) and compositions prepared from the emulsifiable concentrates of the test compounds are sprayed onto the surface of the sand (pre-emergent treatment) and three weeks after sowing (post-emergent treatment). The plastic boxes are watered in a glass house. The results of the treatment are evaluated after a test period of four weeks and assessed with the aid of a scale from 0 to 10, wherein 0=no symtoms and 10=completely destroyed infected plants (100%).

The test results are summarized in Table IV. In the last column of the Table the relative surplus effect (Tr) of the compound 4 related to the compound 6 is given. (Calculation of the relative surplus effect: the activity of compound 6 is subtracted from the activity of compound 4 and the difference is divided by the activity of the compound 6 and multiplied by 100).

TABLE IV

Tests comparing the acitvity of compounds No. 4 and 6

| Weeds | Dose (kg/ha active ingredient) | Compound No. 4 pre | post | Compound No. 6 pre | post | Tr (%) pre | post |
|---|---|---|---|---|---|---|---|
| Amaranthus retroflexus | 0.25 | 7 | 8 | 1 | 2 | 600 | 600 |
|  | 0.5 | 10 | 10 | 3 | 3 | 233 | 233 |
|  | 1.0 | 10 | 10 | 4 | 5 | 150 | 100 |
|  | 2.0 | 10 | 10 | 7 | 7 | 43 | 43 |
| Ohenopodium album | 0.25 | 8 | 8 | 2 | 1 | 300 | 700 |
|  | 0.5 | 10 | 10 | 4 | 3 | 150 | 233 |
|  | 1.0 | 10 | 10 | 6 | 5 | 67 | 100 |
|  | 2.0 | 10 | 10 | 8 | 7 | 25 | 43 |
| Datura Strenorium | 0.25 | 7 | 7 | 1 | 1 | 600 | 600 |
|  | 0.5 | 10 | 10 | 3 | 3 | 233 | 233 |
|  | 1.0 | 10 | 10 | 5 | 6 | 100 | 67 |
|  | 2.0 | 10 | 10 | 7 | 7 | 43 | 43 |
| Erigeron canadensis | 0.25 | 8 | 7 | 2 | 1 | 600 | 600 |
|  | 0.5 | 10 | 10 | 3 | 2 | 233 | 400 |
|  | 1.0 | 10 | 10 | 5 | 5 | 100 | 100 |
|  | 2.0 | 10 | 10 | 7 | 7 | 43 | 43 |
| Xanthium Spinosum | 0.25 | 7 | 7 | 1 | 1 | 600 | 600 |
|  | 0.5 | 10 | 10 | 3 | 3 | 233 | 233 |
|  | 1.0 | 10 | 10 | 5 | 6 | 100 | 67 |
|  | 2.0 | 10 | 10 | 7 | 8 | 43 | 25 |

The data of the Table show that compound No. 4 has a considerably greater activity as it caused a total weed killing even at a dose of 0.25 kg/ha, whereas compound No. 6 does not ensure a 100% weed killing even at an eight-fold dose. There is a considerable difference in activity between the compounds also in the case of monocotyledonous plants. According to our tests compound No. 6 ensures in pre-emergent treatment 85% and in post-emergent treatment 95% protection against Alopecurus myosuroides at a dose of 3 kg/ha, while compound No. 4 ensures a 100% weed killing even at half that dose.

We claim:

1. A compund of the Formula (I)

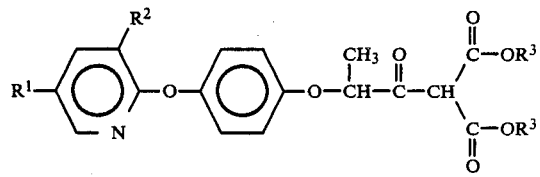

wherein
$R^1$ is hydrogen, halogen, trifluoromethyl, trifluoromethoxy or cyano;
$R^2$ is hydrogen, halogen, or methyl; and
$R^3$ is $C_1$ to $C_4$ alkyl, and the $R^3$ substituents may be the same or different.

2. The compound of the Formula (I) defined in claim 1 which is diethyl-2-[4'-(5''-trifluoromethyl-2''-pyridyloxy)-phenoxy]-propionyl malonate.

3. A herbicidal composition comprising as active ingredient in an amount of 0.01 to 95% by weight a compound of the Formula (I) as defined in claim 1, in admixture with an herbicidally inert solid or liquid carrier.

4. A method for controlling weeds which comprises the step of applying to a plant site in need of said treatment, an herbicidally effective amount of the compound of the Formula (I) defined in claim 1.

* * * * *